(12) United States Patent
She (10) Patent No.: US 11,213,304 B2
(45) Date of Patent: Jan. 4, 2022

(54) SURGERY GUIDING BONE PLATE

(71) Applicant: Cheng Xin She, Kaohsiung (TW)

(72) Inventor: Cheng Xin She, Kaohsiung (TW)

( * ) Notice: Subject to any disclaimer, the term of this patent is extended or adjusted under 35 U.S.C. 154(b) by 75 days.

(21) Appl. No.: 15/580,725

(22) PCT Filed: Jun. 9, 2015

(86) PCT No.: PCT/CN2015/081084
§ 371 (c)(1),
(2) Date: Dec. 8, 2017

(87) PCT Pub. No.: WO2016/197327
PCT Pub. Date: Dec. 15, 2016

(65) Prior Publication Data
US 2018/0161048 A1   Jun. 14, 2018

(51) Int. Cl.
*A61F 5/00* (2006.01)
*A61B 17/17* (2006.01)
*A61C 7/02* (2006.01)
*A61C 1/08* (2006.01)
*A61B 17/15* (2006.01)
*A61B 17/80* (2006.01)
*A61C 7/00* (2006.01)

(52) U.S. Cl.
CPC .......... *A61B 17/176* (2013.01); *A61B 17/151* (2013.01); *A61B 17/171* (2013.01); *A61B 17/8071* (2013.01); *A61C 1/084* (2013.01); *A61C 7/02* (2013.01); *A61C 7/00* (2013.01)

(58) Field of Classification Search
None
See application file for complete search history.

(56) References Cited

U.S. PATENT DOCUMENTS

| | | | |
|---|---|---|---|
| 2010/0145386 A1* | 6/2010 | Greenhalgh | A61B 17/8085 606/246 |
| 2012/0277749 A1* | 11/2012 | Mootien | A61B 17/663 606/70 |

* cited by examiner

*Primary Examiner* — Sameh R Boles
(74) *Attorney, Agent, or Firm* — Raymond Chan (57) ABSTRACT

A surgery guiding bone plate comprises a guiding bone plate. The guiding bone plate comprises a first bone plate and a second bone plate, wherein a guiding groove is formed between the first bone plate and the second bone plate. The surgery guiding bone plate also comprises a fixing and clamping device connected to the first bone plate and the second bone plate. The fixing and clamping device can clamp and fix a flap opening-up instrument, and can guide a doctor to a preset cutting position and a drilling position by means of the guiding bone plate, so as to improve the precision of surgery positioning.

20 Claims, 6 Drawing Sheets

SURGERY GUIDING BONE PLATE

CROSS REFERENCE OF RELATED APPLICATION

This is a U.S. National Stage under 35 U. S.C. 371 of the International Application Number PCT/CN2015/081084, filed Jun. 9, 2015. The afore-mentioned patent application is hereby incorporated by reference in its entirety.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a surgery guiding bone plate, particularly, the present invention relates to a surgery guiding bone plate device used in dental surgery, orthognathic surgery and facial bone contouring surgery.

Description of Related Arts

Orthognathic surgery is well-known for amending orthognathic and facial configuration and fixing problems in growth and development, improving sleep apnea, easing temporomandibular joint and muscle disorders (TMJ disorders), adjusting malocclusion led by bone problems, or performing surgeries when an orthodontic treatment is not able to rectify easily by dental braces; in addition, orthognathic surgery is also performed to treat congenital conditions such as cleft lip and cleft palate. Orthognathic surgery is performed by an oral and maxillofacial surgeon in collaboration with an orthodontist. When an orthognathic surgery is performed, the original palatine bone is cut open, adjusted, and then re-joined by using bone plates and bone nails for shaping, during which medical materials such as metal bone plates, screws, bone nails, or stainless wires are often required, so that the orthognathic and facial areas can be fixed and shaped. However, there is no guiding plate or fixing plate existing currently to completely adhere to the cut section, hence, the surgeon and the orthodontist will need to mark based on experience the cut location by hand and perform the cutting. It is not rare to find that a patient suffers from malocclusions after the surgery, for example, fail to reach to a predetermined biting location, overbite, or poor bite, which may be led by a prolonged surgery or improper experiences, particularly in using a fixing bone plate to rectify palatine bone.

A publicized patent application, TW201313207 titled as "Hinged fixation devices for combined upper jaw correction", claims the fixation device comprising: a first footplate including a first footplate body configured to be attached to a first bone portion; a second footplate including a second footplate body configured to be attached to a second bone portion; and a joining element coupled between the first and second footplate bodies, the joining element including a hinge that defines a pivot axis about which the first footplate body is passively rotatable with respect to the second footplate body in response to a force applied to the second footplate body. As disclosed in TW201313207, the joined angle between the plate and the bone is adjusted by rotating the hinge, which cannot precisely make sure of the location for cutting and the drilling position for the fixing bone plate as well. Therefore, TW201313207 is not able to align precisely the bone plate with the bone for a secured fixation as it cannot align precisely based on morphological characteristics of bones.

A publicized patent application, TW201404364 titled as "Orthodontic treatment anchoring module and correcting board and surgical navigating device thereof", claims the module comprising two bone screws and a correcting board. Each bone screw has an exposed section and an implanted section which communicate with each other. The exposed section of the bone screw has a first pivot-locking portion, a closing portion and a second pivot-locking portion, with the first pivot-locking portion is adjacent to the implanted section of the bone screw, with the closing portion is set between the first pivot-locking portion and the second pivot-locking portion. The peripheral surface of the first pivot-locking portion is non-circle. The correcting board has a bridge-connecting section, a positioning section and a slew-closing section, with the bridge-connecting section is set between the positioning section and the slew-closing section, with the bridge-connecting section has at least one hooking portion, with the positioning section and the slew-closing section receives with the closing portion of the two bone screws. The two bone screws are guided and screwed into appropriate position of the jawbone by operating with a surgical navigating device, to make the correcting board couple with the two bone screws. As disclosed in TW201404364, the correcting board and the bone screws are not able to adjust the location of cutting, furthermore, they cannot adjust the angle of the fixing bone plate to have the fixing bone plate precisely joined with bone, which possibly makes the patient to suffer from incorrect biting, overbite, poor bite and etc. after the surgery.

Therefore, the invention aims at providing a surgery guiding bone plate capable of being used in dental surgery, orthognathic surgery and facial bone contouring surgery. In a upper/lower jaw surgery and a cheek bones surgery, the invention is able to precisely locate the cutting and drilling positions, thereby solving aforementioned problems in orthognathic surgery, that is, the oral and maxillofacial surgeon and the orthodontist can only make certain of the cutting position and the drilling position based on experiences.

SUMMARY OF THE PRESENT INVENTION

One purpose of the invention is to provide a surgery guiding bone plate, which can be used in dental surgery, orthognathic surgery and facial bone contouring surgery, and can precisely make certain of guiding cutting position and drilling position on the upper/lower jaw or cheek bones by using the surgery guiding bone plate.

Another purpose of the invention is to provide a surgery guiding bone plate, which has a fixing and clamping device to assist the oral and maxillofacial surgeon and the orthodontist to operate a flap opening-up instrument, thereby avoiding bone shift caused by a failure of fixing the flap opening-up instrument, hence, the invention increases the degree of precision in locating a cutting position.

To achieve aforementioned purposes, the invention provides a surgery guiding bone plate, which includes a guiding bone plate having a first bone plate and a second bone plate, wherein a guiding groove is arranged between the first bone plate and the second bone plate; and a fixing and clamping device, which connects to the first bone plate and the second bone plate, respectively.

In one embodiment disclosed in the invention, the surgery guiding bone plate is further arranged with one or more locking sections to penetrate the first and second bone plates.

In one embodiment disclosed in the invention, each locking section may be an opening or a screw hole.

In one embodiment, the first bone plate may be a plane bone plate or a curved bone plate.

In one embodiment, the second bone plate may be a plane bone plate or a curved bone plate.

In one embodiment, the guiding bone plate may be made of medical titanium alloys or bioabsorbable materials.

In one embodiment, the fixing and clamping device may be made of medical titanium alloys or bioabsorbable materials.

In one embodiment, the guiding groove may be an opening or a gap.

In one embodiment, the fixing and clamping device may be a suspension loop, a hanging hook, a C-shaped hook, or an L-shaped hook.

In one embodiment, the guiding bone plate, the fixing and clamping device are individually made by using laser metal additive technique or 3D metal printing technique.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

DETAILED DESCRIPTION OF THE PREFERRED EMBODIMENT

Although some words has been used in the specification and subsequent claims to refer to particular components, person having ordinary skill in the art will appreciates that manufacturers may use different terms to refer to a component. The specification and claims are not to be differences in the names as a way to distinguish between the components, but with differences in the function of the component as a criterion to distinguish. As mentioned throughout the specification and claims, in which the "include, has, comprise, and with" are an open-ended term, they should be interpreted as "including but not limited to".

Figure 1:
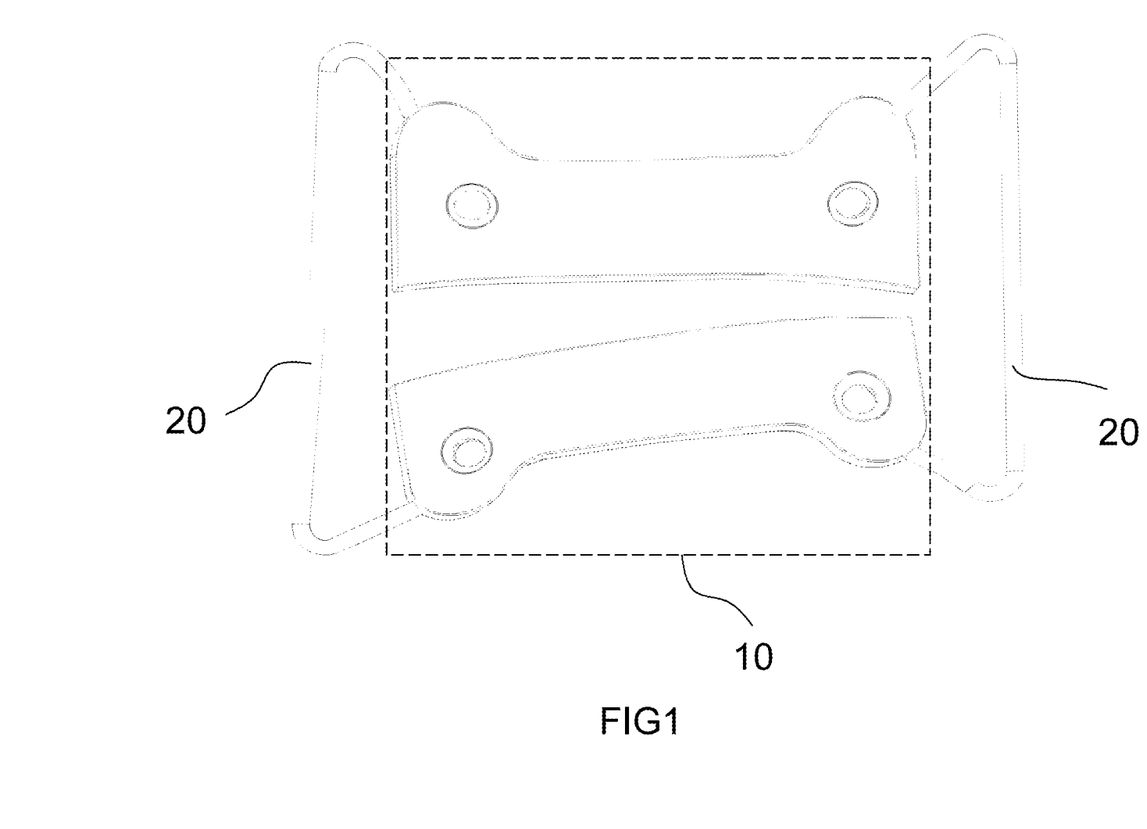
FIG. 1 is a plan schematic diagram of the surgery guiding bone plate
Figure 2:
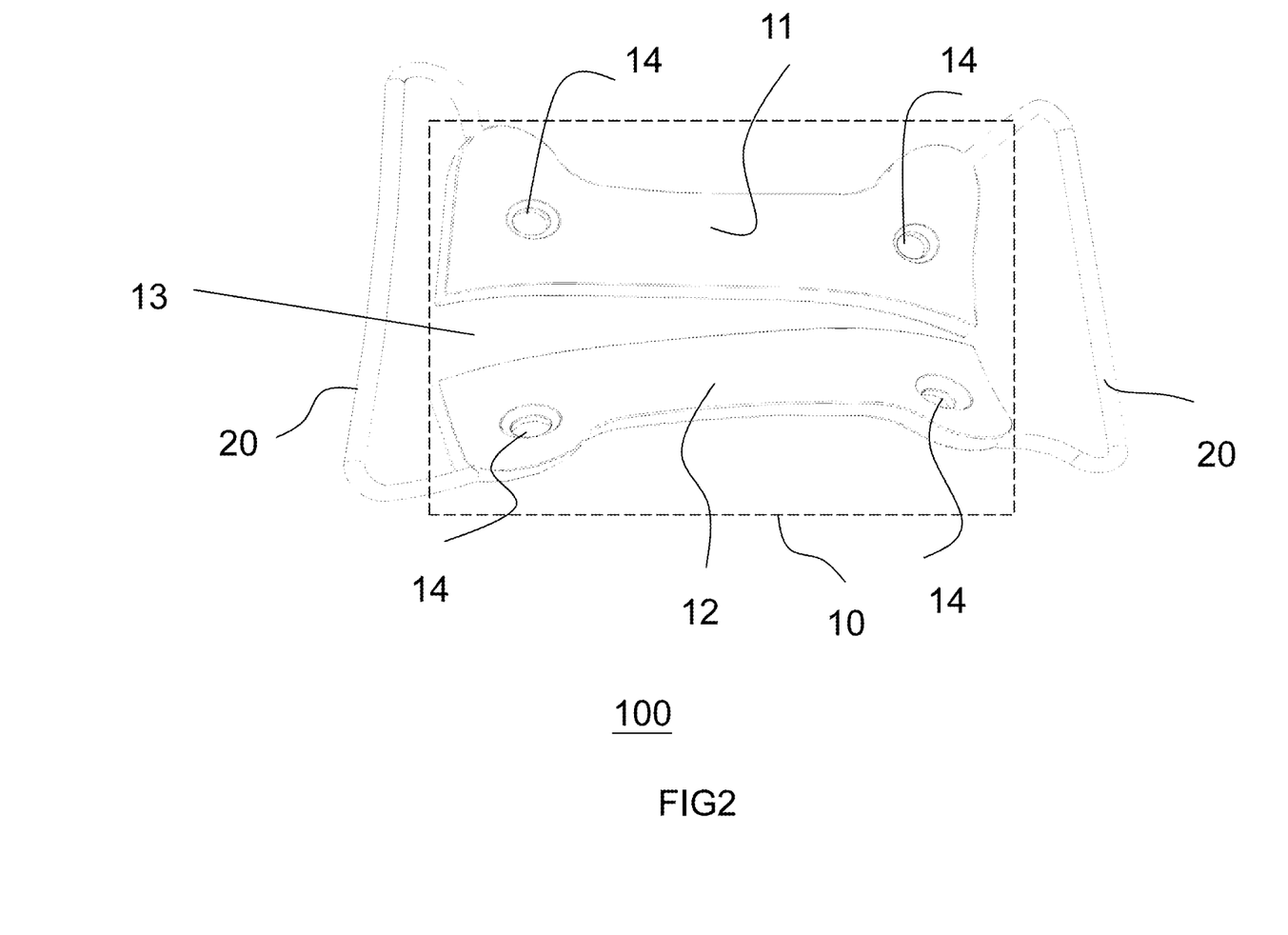
FIG. 2 is a plan schematic diagram of the surgery guiding bone plate

One preferred embodiment discloses a surgery guiding bone plate 100, as shown in FIG. 1 and FIG. 2 which illustrate plan schematic diagrams of the surgery guiding bone plate 100, including a guiding bone plate 10, a first bone plate 11 and a second bone plate 12, wherein a guiding groove 13 is arranged between the first bone plate 11 and the second bone plate 12; furthermore, the surgery guiding bone plate 100 also includes a fixing and clamping device 20, which connects to the first bone plate 11 and the second bone plate 12, respectively.

As shown in FIG. 2, the surgery guiding bone plate 100 is installed with one or more locking sections 14 penetrating the first bone plate 11 and the second bone plate 12, wherein the locking sections 14 may be an opening. When an orthognathic surgery is performed, the locking sections 14 on the surgery guiding bone plate can be used as drilling positions on the upper and lower jaws and cheek bones, and then use bone nails to lock and fix the bone plate for adjustment. The guiding groove 13 arranged between the first bone plate 11 and the second bone plate 12, which may be a gap, is used for assisting and guiding the oral and maxillofacial surgeon and the orthodontist to find preset cutting locations when operating scalpels to cut open the upper/lower jaw and cheek bones, thereby avoiding errors in locating cut positions.

Figure 3:
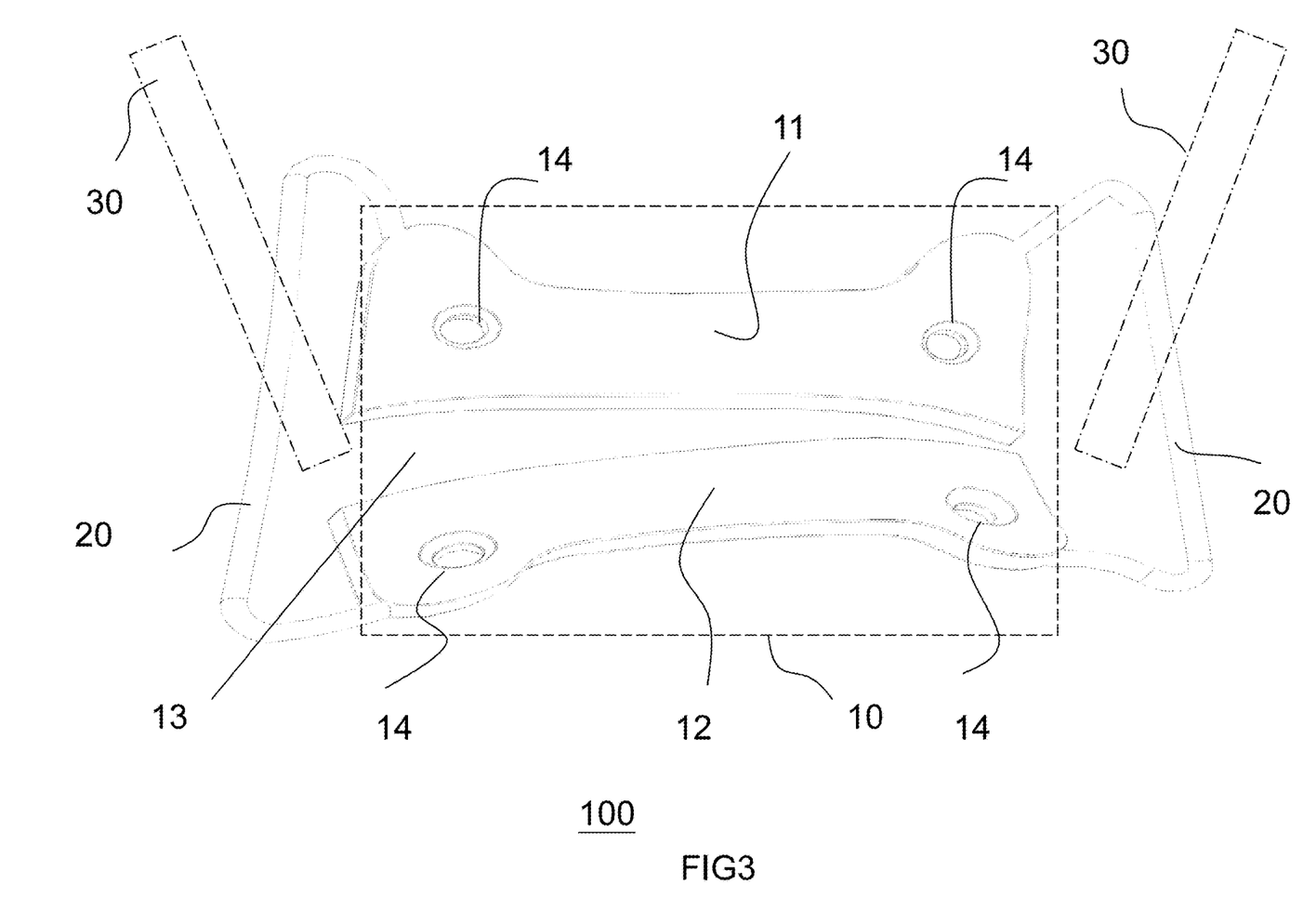
FIG. 3 is a combined schematic diagram of a combined device combining the surgery guiding bone plate with the flap opening-up instrument

As shown in FIG. 3, the combined schematic diagram of a combined device illustrates a combination of the surgery guiding bone plate 100 and the flap opening-up instrument 30. The surgery guiding bone plate 100 includes a fixing and clamping device 20, wherein the fixing and clamping device 20 has a hook-like appearance. When the oral and maxillofacial surgeon and the orthodontist cut the upper/lower jaw and cheek bones, the fixing and clamping device 20 is used to clamp and secure the flap opening-up instrument 30, thereby preventing the flap opening-up instrument 30 from failing to secure during the surgery which results in bone shift in terms of finding preset positions, therefore, errors in locating cutting positions can be prevented.

Figure 4:
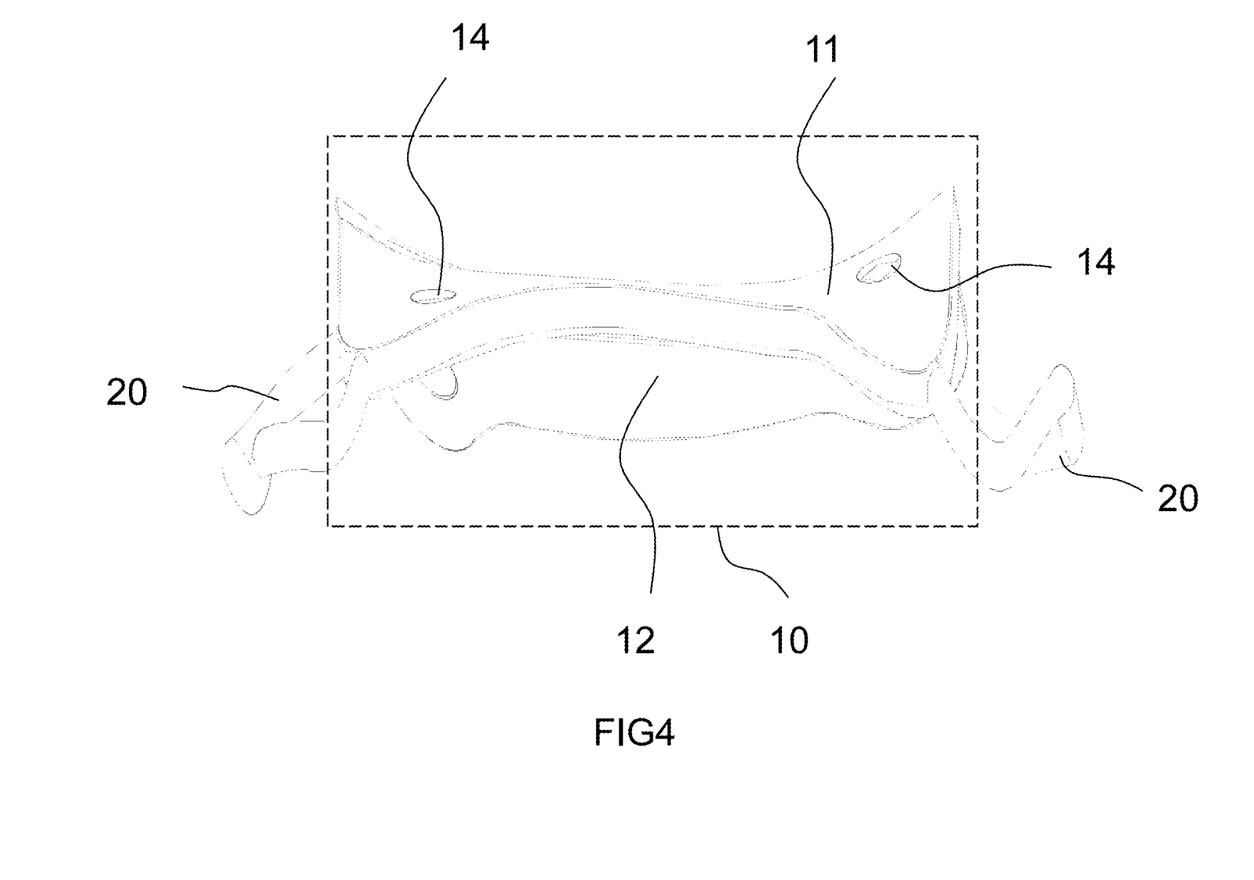
FIG. 4 is a 3D schematic diagram of the surgery guiding bone plate

As shown in FIG. 4, the 3D schematic diagram of the surgery guiding bone plate illustrates the surgery guiding bone plate 100 including a guiding bone plate 10 and a fixing and clamping device 20, which is connected to the first bone plate 11 and the second bone plate 12, respectively. The first bone plate 11 and the second bone plate 12 are in curved appearance, respectively, so that the first bone plate 11 and the second bone plate 12 can tightly join with the upper/lower jaw and cheek bones at preset locations. Moreover, the first bone plate 11 and the second bone plate 12 guide the oral and maxillofacial surgeon and the orthodontist to find preset cutting positions when operating scalpels to cut open the upper/lower jaw and cheek bones. The first bone plate 11 and the second bone plate 12 can use computing software of a custom graphical user interface (GUI) to calculate the change of angle with curvature and gradient. The computing software of a custom graphical user interface (GUI) can be of commercial products such as GRASSHOPPER to calculate axial positions of X, Y, Z and angles, furthermore, the first bone plate 11, the second bone plate 12 and the fixing and clamping device 20 can use laser metal additive technique to manufacture.

According to the embodiment, the guiding bone plate 10 may be made of medical titanium alloys (Ti-6AI-4V), and the fixing and clamping device 20 may be made of medical titanium alloys (Ti-6AI-4V) as well.

According to the embodiment, the first bone plate 11 and the second bone plate 12 may be both replaced by a plane bone plate, the guiding groove 13 may be replaced by an opening, the locking sections 14 may be replaced by a screw hole, the fixing and clamping device 20 may be replaced by a suspension loop, a hanging hook, a C-shaped hook, or an L-shaped hook, the guiding bone plate 10 may be replaced by bioabsorbable materials, the fixing and clamping device 20 may be replaced by bioabsorbable materials, and the guiding bone plate 10 and the fixing and clamping device 20 may be manufactured by 3D metal printing technique.

Figure 5:
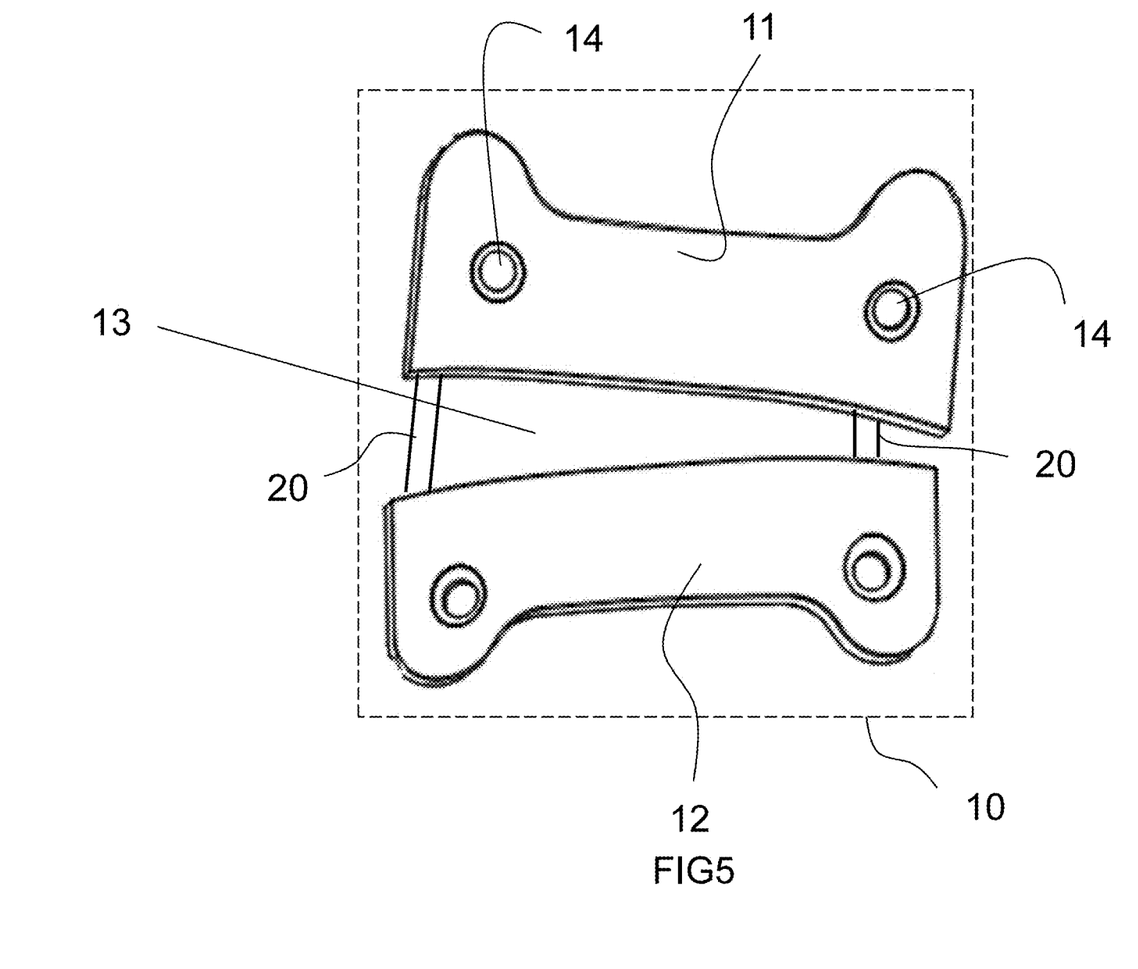
FIG. 5 is a plan schematic diagram of one embodiment for the surgery guiding bone plate

Another preferred embodiment as shown in FIG. 5, which is a plan schematic diagram of the surgery bone plate 100, illustrates that the surgery guiding bone plate 100 includes a guiding bone plate 10, a first bone plate 11 and a second bone plate 12, and a fixing and clamping device 20; wherein the first bone plate 11 and the second bone plate 12 has one or more locking sections 14, and the fixing and clamping device 20 connects to one side of the first bone plate 11 and the second bone plate 12, respectively. The first bone plate 11, the second bone plate 12 and the fixing and clamping device 20 are arranged with a guiding groove 13 therein, thereby enabling the oral and maxillofacial surgeon and the orthodontist to be guided to preset cutting positions when operating scalpels to cut open the upper/lower jaw and cheek bones through the guiding groove 13.

Figure 6:
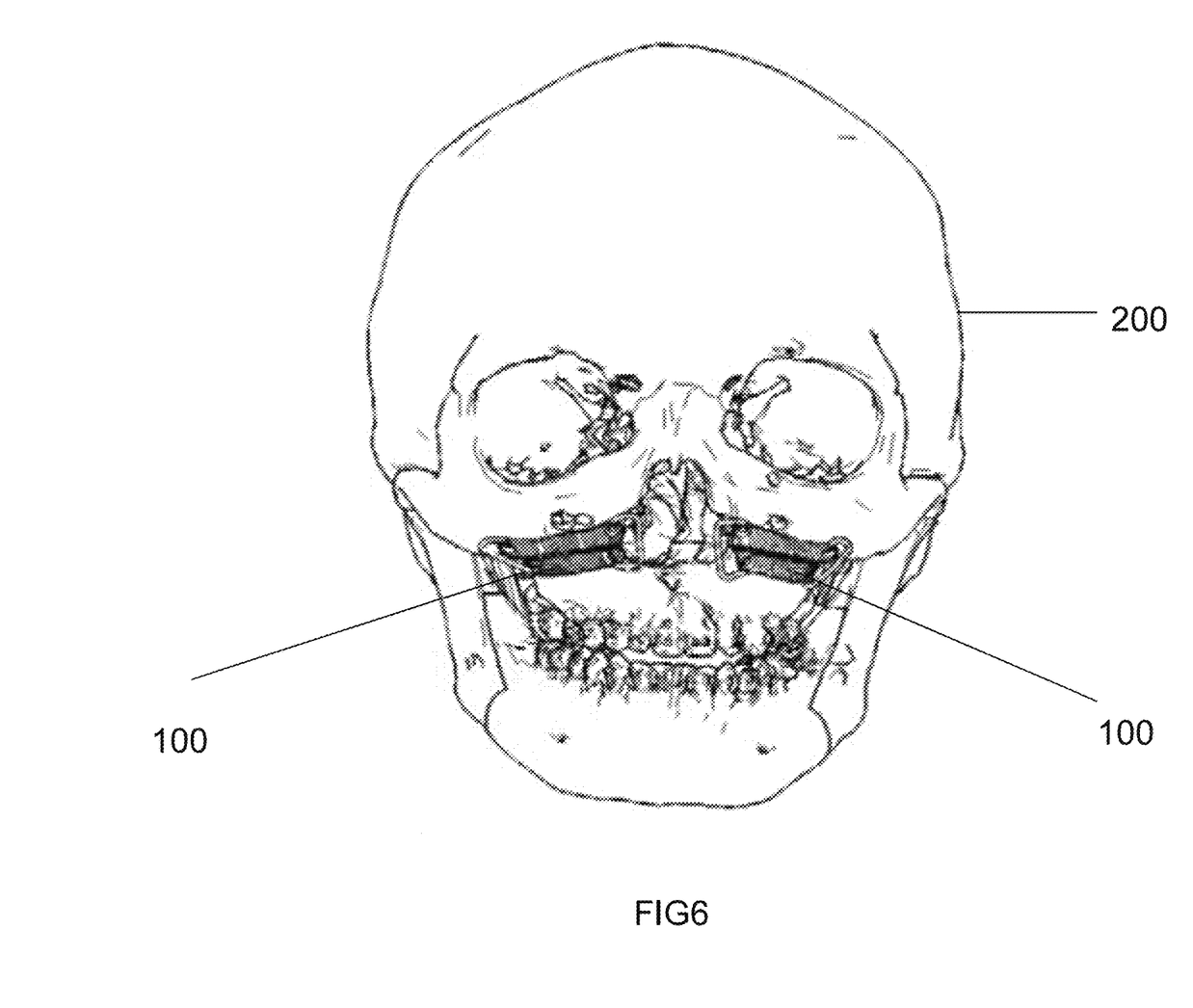
FIG. 6 is a combined schematic diagram of the surgery guiding bone plate combining with human bone.

Another preferred embodiment as shown in FIG. 6 is a combined schematic diagram of the surgery guiding bone plate being used on a human. When an orthognathic surgery is performed, the original palatine bone is cut open, adjusted, and then re-joined by using bone plates and bone nails for shaping. As shown in FIG. 6, the surgery guiding bone plate 100 can be combined with the upper/lower jaw and cheek bones of a human skull 200. When the oral and maxillofacial surgeon and the orthodontist use scalpels to cut the upper/lower jaw and cheek bones at preset positions, the surgery guiding bone plate 100 can further precisely guide them to the drilling positions on the upper/lower jaw and cheek bones, thereby enabling them to use bone nails to secure bone plate onto preset positions.

There have thus been shown and described a surgery guiding bone plate. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention.

What is claimed is:

1. A surgery guiding bone plate for incorporating with a flap opening-up instrument during dental surgery, orthognathic surfery or facial bone contouring surgery for locating a preset cutting location on a facial bone of a user, comprising:
    a guiding bone plate which comprises a first bone plate and a second bone plate and has one or more locking sections and a guiding groove, wherein said first bone plate and said second bone plate are configured for affixing at facial bones of a user, wherein changes of angles with curvatures and gradients of said first first bone plate and said second bone plate are calculated for matching with the facial bones of the user, wherein said first bone plate and said second bone plate are manufactured based on changes of angles with curvatures and gradients, wherein said one or more locking sections are formed at each of said first bone plate and said second bone plate for precisely providing predetermined drilling locations on the facial bone by said one or more locking sections, wherein said guiding groove is a gap formed between said first bone plate and said second bone plate along inner walls of said first bone plate and said second bone plate and located at preset cutting location of the facial bone when said first bone plate and said second bone plate are affixed to the facial bones; and
    two fixing and clamping devices extended from two sides of said first bone plate to two sides of said second bone plate respectively such that said guiding groove is formed within said first bone plate, said second bone plate and said two fixing and clamping devices, wherein said two fixing and clamping devices are arranged for clamping and securing a flap opening-up instrument.

2. The surgery guiding bone plate, as recited in claim 1, wherein each of said fixing and clamping devices is a C-shaped hook coupled between said side of said first bone plate and said side of said second bone plate.

3. The surgery guiding bone plate, as recited in claim 1, wherein each of said locking sections is an opening formed on each of said first bone plate and said second bone plate.

4. The surgery guiding bone plate, as recited in claim 2, wherein each of said locking sections is an opening formed on each of said first bone plate and said second bone plate.

5. The surgery guiding bone plate, as recited in claim 1, wherein each of said locking sections is a screw hole formed on each of said first bone plate and said second bone plate.

6. The surgery guiding bone plate, as recited in claim 2, wherein each of said locking sections is a screw hole formed on each of said first bone plate and said second bone plate.

7. The surgery guiding bone plate, as recited in claim 4, wherein each of said locking sections is a screw hole formed on each of said first bone plate and said second bone plate.

8. The surgery guiding bone plate, as recited in claim 1, wherein each of said first bone plate and said second bone plate is made of medical titanium alloys (Ti-6AI-4V).

9. The surgery guiding bone plate, as recited in claim 2, wherein each of said first bone plate and said second bone plate is made of medical titanium alloys (Ti-6AI-4V).

10. The surgery guiding bone plate, as recited in claim 4, wherein each of said first bone plate and said second bone plate is made of medical titanium alloys (Ti-6AI-4V).

11. The surgery guiding bone plate, as recited in claim 7, wherein each of said first bone plate and said second bone plate is made of medical titanium alloys (Ti-6AI-4V).

12. The surgery guiding bone plate, as recited in claim 1, wherein said first bone plate, said second bone plate, and said two fixing and clamping devices are manufactured by a laser metal additive process.

13. The surgery guiding bone plate, as recited in claim 4, wherein said first bone plate, said second bone plate, and said two fixing and clamping devices are manufactured by a laser metal additive process.

14. The surgery guiding bone plate, as recited in claim 7, wherein said first bone plate, said second bone plate, and said two fixing and clamping devices are manufactured by a laser metal additive process.

15. The surgery guiding bone plate, as recited in claim 11, wherein said first bone plate, said second bone plate, and said two fixing and clamping devices are manufactured by a laser metal additive process.

16. The surgery guiding bone plate, as recited in claim 1, wherein said first bone plate, said second bone plate, and said two fixing and clamping devices are manufactured by a 3D metal printing process.

17. The surgery guiding bone plate, as recited in claim 4, wherein said first bone plate, said second bone plate, and said two fixing and clamping devices are manufactured by a 3D metal printing process.

18. The surgery guiding bone plate, as recited in claim 7, wherein said first bone plate, said second bone plate, and said two fixing and clamping devices are manufactured by a 3D metal printing process.

19. The surgery guiding bone plate, as recited in claim 11, wherein said first bone plate, said second bone plate, and said two fixing and clamping devices are manufactured by a 3D metal printing process.

20. The surgery guiding bone plate, as recited in claim 15, wherein said first bone plate, said second bone plate, and said two fixing and clamping devices are manufactured by a 3D metal printing process.

\* \* \* \* \*